United States Patent
Mizukami et al.

(10) Patent No.: US 11,734,824 B2
(45) Date of Patent: Aug. 22, 2023

(54) IMAGE PROCESSING METHOD, DRUG SENSITIVITY TEST METHOD AND IMAGE PROCESSING APPARATUS

(71) Applicant: FRONTIER PHARMA INC., Shiga (JP)

(72) Inventors: Tamio Mizukami, Shiga (JP); Katsumi Kishimoto, Shiga (JP)

(73) Assignee: FRONTIER PHARMA INC., Shiga (JP)

( * ) Notice: Subject to any disclaimer, the term of this patent is extended or adjusted under 35 U.S.C. 154(b) by 493 days.

(21) Appl. No.: 17/059,500

(22) PCT Filed: May 17, 2019

(86) PCT No.: PCT/JP2019/019666
§ 371 (c)(1),
(2) Date: Nov. 30, 2020

(87) PCT Pub. No.: WO2019/230447
PCT Pub. Date: Dec. 5, 2019

(65) Prior Publication Data
US 2021/0224992 A1 Jul. 22, 2021

(30) Foreign Application Priority Data

Jun. 1, 2018 (JP) .................................. 2018-105777
May 10, 2019 (JP) .................................. 2019-089529

(51) Int. Cl.
*G06K 9/00* (2022.01)
*G06T 7/00* (2017.01)
(Continued)

(52) U.S. Cl.
CPC .......... *G06T 7/0014* (2013.01); *G06N 20/00* (2019.01); *G06T 7/74* (2017.01); *G16H 20/10* (2018.01);
(Continued)

(58) Field of Classification Search
CPC .......... G01N 2500/10; G01N 33/5008; G01N 33/5044; G01N 2015/1006; G01N 15/10;
(Continued)

(56) References Cited

U.S. PATENT DOCUMENTS

2017/0169567 A1* 6/2017 Chefd'hotel .......... G06T 7/0012
2018/0286038 A1* 10/2018 Jalali .................... G01N 15/147
(Continued)

FOREIGN PATENT DOCUMENTS

JP 2015-521037 A 7/2015
JP 2017-045341 A 3/2017
(Continued)

OTHER PUBLICATIONS

International Search Report issued in corresponding International Patent Application No. PCT/JP2019/019666, dated Aug. 13, 2019, with English translation.

(Continued)

*Primary Examiner* — Atiba O Fitzpatrick
(74) *Attorney, Agent, or Firm* — McDermott Will & Emery LLP

(57) ABSTRACT

An image processing method is configured to input a test image to a first learning model, input an output image to a second learning model and output an output image as a result image in which the position of the detected part is indicated by a representative point. The first learning model is constructed by deep learning using teacher data associating a first image in which a marker is expressed and a second image in which the marker is not expressed. The first and the second images are captured to include a same cell. The second learning model is constructed by deep learning using teacher data associating a third image, which is captured to include a cell and in which the marker is expressed, and (Continued)

information representing a position of the representative point included in the third image.

10 Claims, 11 Drawing Sheets

(51) Int. Cl.
    *G06T 7/73*     (2017.01)
    *G16H 20/10*     (2018.01)
    *G16H 30/40*     (2018.01)
    *G06N 20/00*     (2019.01)

(52) U.S. Cl.
    CPC ... *G16H 30/40* (2018.01); *G06T 2207/10064* (2013.01); *G06T 2207/20081* (2013.01); *G06T 2207/30024* (2013.01)

(58) Field of Classification Search
    CPC .............. G01N 15/1475; C12M 41/46; G06T 2207/10056; G06T 2207/10061; G06T 2207/30024; G06T 2207/20081; G06T 2207/20084; G06T 11/00; G06T 2211/00; G06T 2207/10064; G06T 2207/20112; G06T 7/11; G06T 7/155; G06T 7/174; G06T 7/187; G06T 7/194; G06T 7/70; G06T 2207/30242; G06V 20/69–698; G06V 2201/04; G06V 10/70; G06V 10/82; G06V 10/774–7796; G06V 10/87; G06V 30/19113; G06V 10/25; G06V 10/764; G06V 20/695; G06K 9/6256; G06K 9/6257; G06K 9/6259; G06N 3/02–126; G06N 20/00–20; G06N 3/045; G06N 3/0455; G06N 3/0475; G06F 18/214–2155; G06F 7/023; G06F 40/16; A61B 5/0275; A61B 5/02755
    See application file for complete search history.

(56) References Cited

U.S. PATENT DOCUMENTS

| | | | |
|---|---|---|---|
| 2019/0012521 | A1 | 1/2019 | Cohen |
| 2019/0156476 | A1* | 5/2019 | Yoshida ................ G06T 7/0012 |
| 2019/0294930 | A1* | 9/2019 | Koike ...................... G06N 3/08 |
| 2019/0384047 | A1* | 12/2019 | Johnson ................... G06N 3/08 |
| 2020/0257886 | A1 | 8/2020 | Fujimoto et al. |
| 2021/0173188 | A1* | 6/2021 | Johnson ................. G06V 10/50 |

FOREIGN PATENT DOCUMENTS

| | | |
|---|---|---|
| JP | 2017-85966 A | 5/2017 |
| JP | 2017-516992 A | 6/2017 |
| JP | 2017-519985 A | 7/2017 |
| WO | 2013/166336 A1 | 11/2013 |
| WO | 2015/177268 A1 | 11/2015 |
| WO | 2015/195609 A1 | 12/2015 |
| WO | 2017/027380 A1 | 2/2017 |

OTHER PUBLICATIONS

Niioka, H. et al., "Classification of C2C12 cells at differentiation by convolutional neural network of deep learning using phase contrast images" Human Cell, 2018, vol. 31, No. 1, pp. 87-93.
Takahashi, Sora et al., "[3P-0777] Deep learning-aided label-free cell counting technology: prediction of fluorescent labels from unlabeled cell images", The 41st annual conference of the Molecular Biology Society of Japan, Nov. 30, 2018, with English translation.
Miyaki, Akira, "P7. Development of live/death identification and counting technique for label-free and noninvasive cells by deep learning", The 9th Annual Conference on Biomolecular Screenology, Nov. 30, 2018, with English translation.
Ono, Kosuke, "P8. Live/death identification and counting technique developed by deep learning for label-free and noninvasive cells, and its application to hepatocyte toxicity assessment", The 9th Annual Conference on Biomolecular Screenology, Nov. 30, 2018, with English translation.
E. Christiansen et al., "In Silico Labeling: Predicting Fluorescent Labels in Unlabeled Images", Cell, Google, Inc., Apr. 19, 2018, vol. 173, pp. 792-803.
P. Isola et al., "Image-to-Image Translation with Conditional Adversarial Networks", CVPR, Nov. 21, 2016, URL: https://arxiv.org/pdf/1611.07004v1.pdf.
Japanese Notice of Reasons for Refusal issued in corresponding Japanese Patent Application No. 2019-089529, dated Aug. 6, 2019, with English translation.
Japanese Notice of Reasons for Refusal issued in corresponding Japanese Patent Application No. 2019-089529, dated Sep. 10, 2019, with English translation.
Miao Yunxiang et al., "Iteratively training classifiers for circulating tumor cell detection", 2015 IEEE 12th International Symposium on Biomedical Imaging (ISBI), IEEE, Apr. 16, 2015 (Apr. 16, 2015), pp. 190-194.
Sajith Kecheril Sadanandan et al., "Automated Training of Deep Convolutional Neural Networks for Cell Segmentation", Scientific Reports, vol. 7, No. 1, Aug. 10, 2017 (Aug. 10, 2017).
Eric M Christiansen et al., "In Silico Labeling: Predicting Fluorescent Labels in Unlabeled Images", Cell, vol. 173, No. 3 Apr. 19, 2018 (Apr. 19, 2018), pp. 792-803.
Chawin Ounkomol et al., "Label-free prediction of three-dimensional fluorescence images from transmitted light microscopy", bioRxiv, May 23, 2018 (May 23, 2018).
Extended European Search Report issued in corresponding European Patent Application No. 19811408.4-1210, dated Feb. 8, 2022.

\* cited by examiner

FIG. 10

| | INPUT IMAGE (BRIGHT FIELD IMAGE) | GENERATED IMAGE (PSEUDO FLUORESCENCE IMAGE) | TARGET IMAGE (COLOR FLUORESCENCE IMAGE) |
|---|---|---|---|
| A | | | |
| B | | | |
| C | | | |
| D | | | |

FIG. 11

| | INPUT IMAGE (BRIGHT FIELD IMAGE) | GENERATED IMAGE (PSEUDO FLUORESCENCE IMAGE) | TARGET IMAGE (COLOR FLUORESCENCE IMAGE) |
|---|---|---|---|
| A | | | |
| B | | | |
| C | | | |
| D | | | |

# IMAGE PROCESSING METHOD, DRUG SENSITIVITY TEST METHOD AND IMAGE PROCESSING APPARATUS

CROSS REFERENCE TO RELATED APPLICATIONS

This application is the U.S. National Phase under 35 U.S.C. § 371 of International Application No. PCT/JP2019/019666, filed on May 17, 2019, which claims the benefit of Japanese Patent Application No. 2018-105777, filed on Jun. 1, 2018 and Japanese Patent Application No. 2019-089529, filed on May 10, 2019, the entire contents of each are hereby incorporated by reference.

TECHNICAL FIELD

This invention relates to an image processing method for determining the positions of specific parts of cells included in an image obtained by imaging the cells, a drug sensitivity test method and an image processing device using the image processing method.

BACKGROUND ART

For example, in an experiment aimed at drug discovery screening, the observation of changes of cells in a specimen, to which a drug is administered, is widely performed. An ATP method, an MTT method and the like are known as conventional test methods. Further, in recent years, the number, sizes, shapes and the like of cells have also been automatically measured from an image obtained by imaging a specimen. In such an experiment, such a marker that will be selectively expressed in a part having a specific property (e.g. a cell nucleus) is introduced into the cells (this operation is also called labeling). Then, expression sites of the marker in the image are detected by an image processing (e.g. see PTL 1).

CITATION LIST

Patent Literature

[PTL 1] JP 2015-521037A

SUMMARY OF INVENTION

Technical Problem

Such marker introduction is to modify the cells as observation objects. Thus, it is not necessarily suitable for the continuous observation of cells. Further, a reagent for administering the marker and a marker introduction operation cause an increase of experiment cost. From this, it is desired to identify cells from an image without using a marker.

Particularly, in an experiment for drug discovery screening, it is desirable to be able to easily grasp how many cells are living, out of various objects included in an image. However, an image captured without using a marker is suitable for the observation of the shapes, textures and the like of cells, but cannot necessarily be said to be suitable to automatically measure the positions and number of the cells. Thus, it is desired to establish a technique for automatically measuring the positions and number of cells from an image captured without using a marker.

Solution to Problem

This invention was developed in view of the above problem and an object thereof is to provide an image processing technique capable of automatically measuring the positions and number of cells included in an image even if the image is captured without using a marker.

One aspect of this invention is directed to an image processing method for detecting a position of a specific detected part from a test image obtained by imaging a cell. To achieve the above object, the image processing method includes inputting the test image to a first learning model, inputting an output image of the first learning model to a second learning model, and outputting an output image of the second learning model as a result image in which the position of the detected part is indicated by a representative point thereof.

Further, another aspect of this invention is directed to an image processing apparatus for detecting a position of a specific detected part from a test image obtained by imaging a cell. To achieve the above object, the image processing apparatus includes an image acquirer for obtaining a bright field image or phase difference image as the test image, and an image processor for inputting the test image to a first learning model, inputting an output image of the first learning model to a second learning model, and outputting an output image of the second learning model as a result image in which the position of the detected part is indicated by a representative point thereof.

In these aspects of the invention, the first learning model is constructed by using teacher data associating a first image and a second image captured to include the same cell and performing deep learning (deep structured learning) with the second image corresponding to an input and the first image corresponding to an output. Here, the first image is an image in which a marker corresponding to the detected part is expressed, and the second image is an image in which the marker is not expressed. Further, the second learning model is constructed by using teacher data associating a third image, which is captured to include the cell and in which the marker is expressed, and information representing a position of the representative point included in the third image and performing deep learning with the third image corresponding to an input and the position of the representative point corresponding to an output.

In the invention thus configured, the position of the detected part having a specific feature can be accurately detected even from the test image into which the marker is not introduced. The reason for that is as follows.

In the invention, the first learning model is a learning model constructed by performing deep learning using the teacher data associating the first image in which the marker corresponding to the detected part is expressed and the second image in which the marker is not expressed. Thus, in the already learned first learning model, an image with a marker and an image without a marker are associated with each other.

Thus, if the test image in which the marker is not expressed is input to the first learning model, an image with a marker corresponding to the test image is obtained as an output of the first learning model. This image is equivalent to an image obtained when the marker is introduced into a specimen used in the imaging of the test image and imaging is performed on a condition that that marker is expressed. That is, the first learning model has a function of generating an image with a pseudo marker, which would be obtained if the same specimen were imaged in a state where the marker is expressed, from a test image without a marker. In this way, even if the marker is not actually introduced into the specimen, an image as if the marker were expressed can be obtained.

On the other hand, the second learning model is a learning model constructed by performing deep learning using the teacher data associating the image in which the marker is expressed and the information representing the position of the representative point of the detected part. Therefore, in the already learned second learning model, the image in which the marker is expressed and the position of the representative point of the detected part included in the image are associated with each other.

Thus, if the image in which the marker is expressed is input to the second learning model, an image showing the position of the representative point of the detected part present in the input image is obtained as an output of the second learning model. Here, if the output image of the first learning model is used as the input image, a final output image specifying the position of the representative point of the detected part in the output image of the first learning model is obtained. The output image of the first learning model is the image with the pseudo marker generated from the test image without the marker. Therefore, by a series of processings described above, the position of the representative point of the detected part in the test image is specified from the test image without the marker.

It has been conventionally performed to classify cell images by supervised machine learning. However, this is done by clustering in a feature amount space based on an artificially selected feature amount in many cases. In these cases, since which feature amount is used influences classification accuracy, the feature amount needs to be determined according to features shown by a detected part and other parts. Therefore, expert knowledge for selecting the feature amount is necessary in operation. Further, a result of learning is not necessarily high in versatility to various cells.

In contrast, in the invention by deep learning, it is not necessary to select a feature amount beforehand. If only sufficient image samples serving as teacher data can be prepared, a highly accurate learning model can be constructed. Thus, various cells different in features appearing in images can be dealt with by the same learning algorithm.

As just described, in the invention, the position of the representative point representing the detected part can be detected with high accuracy. Thus, even from a test image without a marker, the positions and number of detected parts in this image can be automatically measured.

Further, another aspect of this invention is directed to a drug sensitivity test method including obtaining an image by imaging a specimen to which a drug to be evaluated is administered to cultured cells, counting the number of living cells as the detected parts by the above image processing method using the obtained image as the test image, and determining sensitivity of the cells to the drug based on a result of counting.

In the invention thus configured, the above image processing method is performed using the living cells in the test image as the detected parts. In this way, the positions in the test image where the living cells are present can be accurately specified. If this result is used, it is possible to selectively detect the living cells in the test image and accurately obtain the number of the living cells. Therefore, the sensitivity of the cells to the drug can be effectively determined based on the number of the living cells.

Advantageous Effects of Invention

According to the invention, it is possible to accurately detect the positions of representative points of detected parts in a test image without a marker from this test image by using learning models constructed by previous deep learning. Therefore, a result image suitable to automatically measure the positions and number of the detected parts can be output.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF DRAWINGS

FIG. 10 is a picture showing image examples of triply dyed specimens.

FIG. 11 is a picture showing image examples of triply dyed specimens.

DESCRIPTION OF EMBODIMENTS

Figure 1:
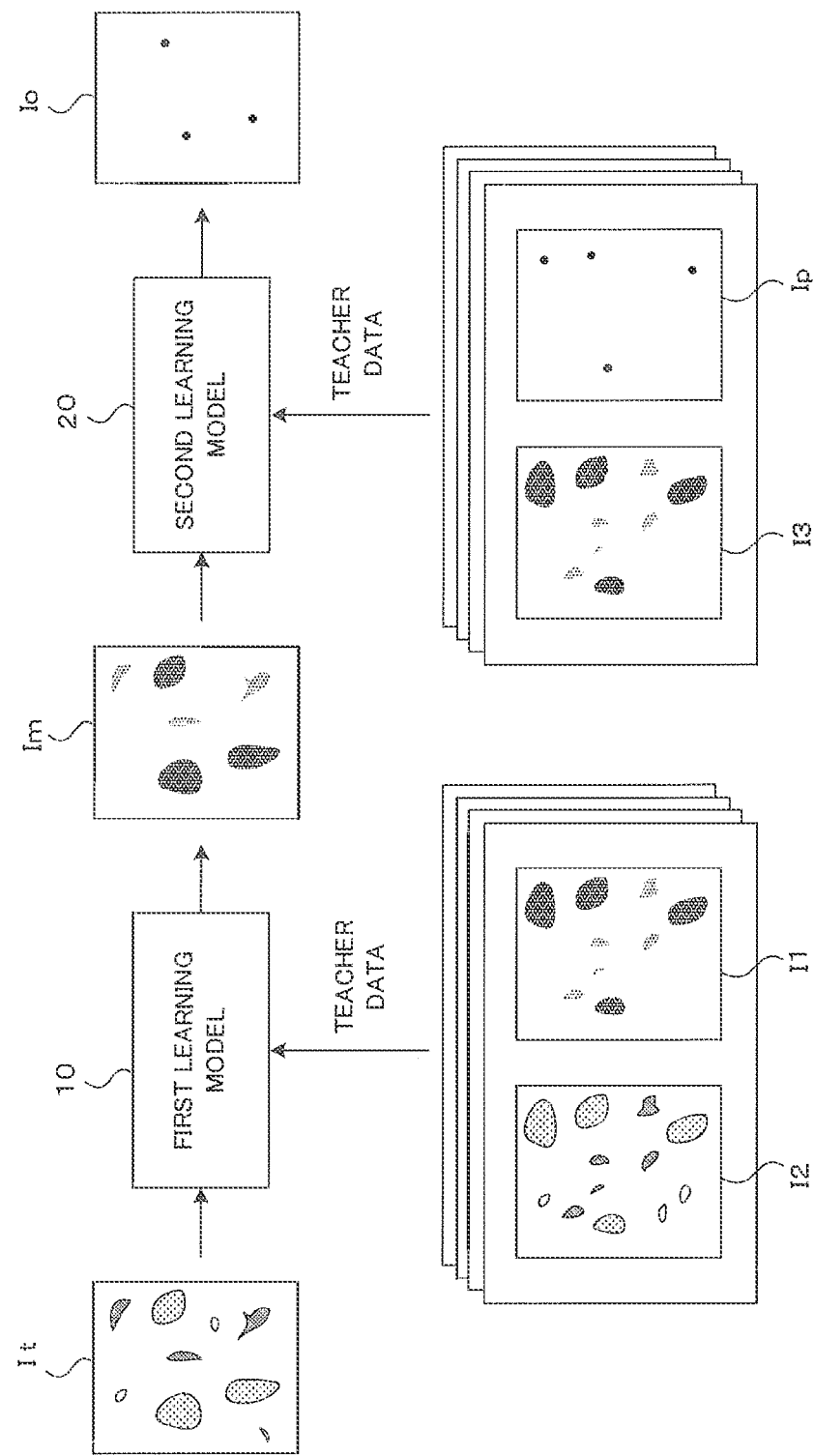
FIG. 1 is a diagram showing a concept of an image processing as one embodiment of the invention.
Figure 2:
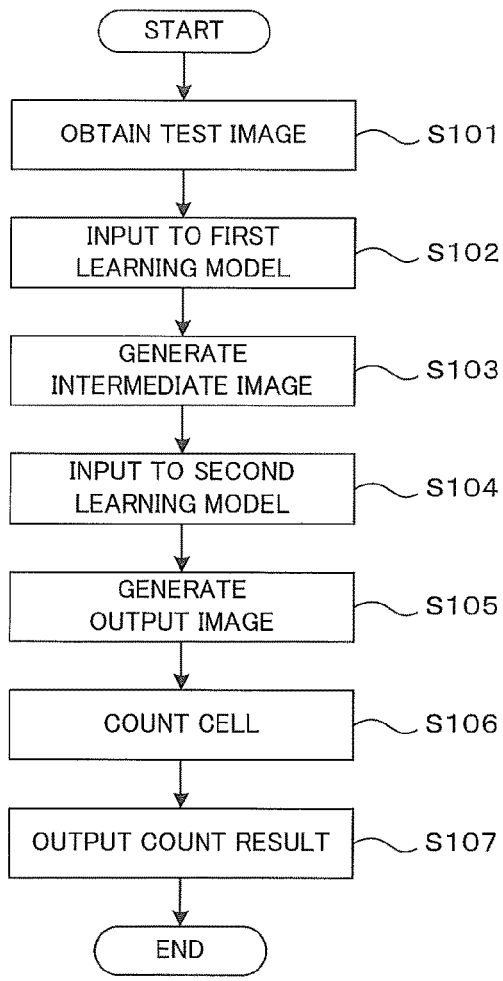
FIG. 2 is a flow chart showing this image processing.

FIG. 1 is a diagram showing a concept of an image processing as one embodiment of the invention. FIG. 2 is a flow chart showing this image processing. The purpose of this image processing is to detect the positions of specific detected parts (e.g. cell nuclei) from a test image It captured to include cells and finally measure the number of the cells satisfying a predetermined condition. More specifically, the test image It as a target is, for example, a bright field image or phase difference image obtained by optical microscope imaging. Further, a detection result of the detected parts is output as a result image Io showing the positions of representative points of the detected parts.

A summary of a specific processing is as follows. First, the test image It as a target is obtained (Step S101). The test image It may be obtained by newly performing imaging. Further, the test image It may be obtained by reading image data captured in advance and stored in an appropriate storage means.

The test image It is input to a first learning model 10 (Step S102). The first learning model 10 outputs an intermediate image Im generated based on the test image It (Step S103). The intermediate image Im is an image which would be obtained if the same sample as the test image It were imaged under a condition that a marker is expressed.

That is, the first learning model 10 has a function of generating the intermediate image Im, to which a pseudo marker is administered, from the test image It without a marker. In this sense, the first learning model 10 can be, for example, called a "marker generation model". If an image with a pseudo marker can be generated with high accuracy (i.e. to have a high degree of similarity to an image actually captured with a marker introduced) from an image without a marker, it is not necessary to introduce a marker into a specimen. This obviates the need for invasive imaging to cells as observation objects and contributes to a reduction of cost associated with marker introduction.

In imaging without introducing a marker, a processing for introducing a marker into a specimen needs not be performed. Thus, non-invasive imaging to cells is possible and this imaging can be applied also for the purpose of observing changes of cells with time. Further, since a reagent serving as a marker and a processing for introducing the reagent are not necessary, experiment cost including the cost of imaging can also be suppressed. Further, depending on the type of the marker, it takes time, for example, several days if it is long, until imaging becomes possible. Such a time can also be eliminated. Thus, this imaging is suitable also for the observation of a specimen in which states of cells largely change in a short time, and suitably applied, for example, to a field of regenerative medicine.

Since the shapes of cells, the shading of internal structures and the like clearly appear in an image not accompanied by a marker and captured in this way, e.g. a bright field image of cells, such an image is suitable for visual observation. On the other hand, for the purpose of quantitatively and automatically detecting the positions and number of specified parts to be noticed, e.g. cell nuclei, in an image, an image with a marker remains to be advantageous in terms of measurement accuracy. Therefore, if an image with a marker can be generated from an image without a marker, an accurate and quantitative measurement is possible even from an image without a marker.

For this purpose, the first learning model 10 is constructed by deep learning using teacher data collected in advance. The teacher data is a collection of a multitude of sets of a first teacher image I1 and a second teacher image I2 obtained by imaging the same position of a specimen prepared in advance to include cells into which a marker is introduced. Here, the first teacher image I1 is obtained by imaging the specimen in which the marker is expressed, and the second teacher image I2 is obtained by imaging the specimen in a state where the marker is not expressed.

A substance that selectively emits fluorescence in a specific part of a cell can be, for example, used as a marker. In this case, a fluorescence image of a specimen imaged under excitation light illumination can be the first teacher image I1, and a bright field image of the same specimen imaged under visible light illumination can be the second teacher image I2. Between such first and second teacher images I1, I2, how an object appears in the image can be related when the same object in the specimen is imaged with a marker and imaged without a marker by comparing corresponding positions in the images.

A multitude of such instances are collected and used as teacher data to perform machine learning. Then, it becomes possible to analogize, for example, how an object appearing in an image without a marker would appear if the object is imaged in a state where a marker is expressed. Utilizing this, it is possible to generate an image with a pseudo marker from an image without a marker. Particularly, when deep learning is used as a learning algorithm, it is not necessary to artificially give a feature amount for the analysis of an image. Thus, expert knowledge for appropriately selecting a feature amount according to use is unnecessary. In addition, it is possible to construct an optimal learning model excluding a possibility of erroneous determination due to inappropriate selection of the feature amount.

Since various publicly known information materials on the principle of deep learning and the learning algorithm already exist, these are not described in detail here. A deep learning technique usable in this embodiment is not limited to a specific algorithm. Note that a method known as "pix2pix" based on Conditional GAN is, for example, a deep learning technique particularly suitably usable in this embodiment for learning a correlation between paired data using the paired data such as images as an input and an output (reference: Phillip Isola et al., Image-to-image Translation with Conditional Adversarial Networks, CVPR, 21 Nov. 2016, URL: https://arxiv.org/pdf/1611.07004v1.pdf).

Figure 3:
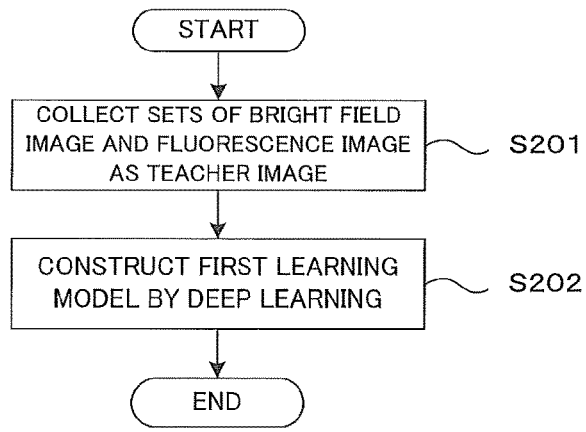
FIG. 3 is a flow chart showing a learning process for constructing the first learning model.

FIG. 3 is a flow chart showing a learning process for constructing the first learning model. As described above, the first learning model 10 can be constructed by collecting a multitude of sets of a bright field image and a fluorescence image obtained by imaging the same position of the same specimen (Step S201) and performing deep learning using these as teacher data (Step S202). The teacher images (first teacher image I1 and second teacher image I2) are desirably images obtained by imaging the same type of cells as cells including detected parts to be noticed in the test image It.

Figure 4:
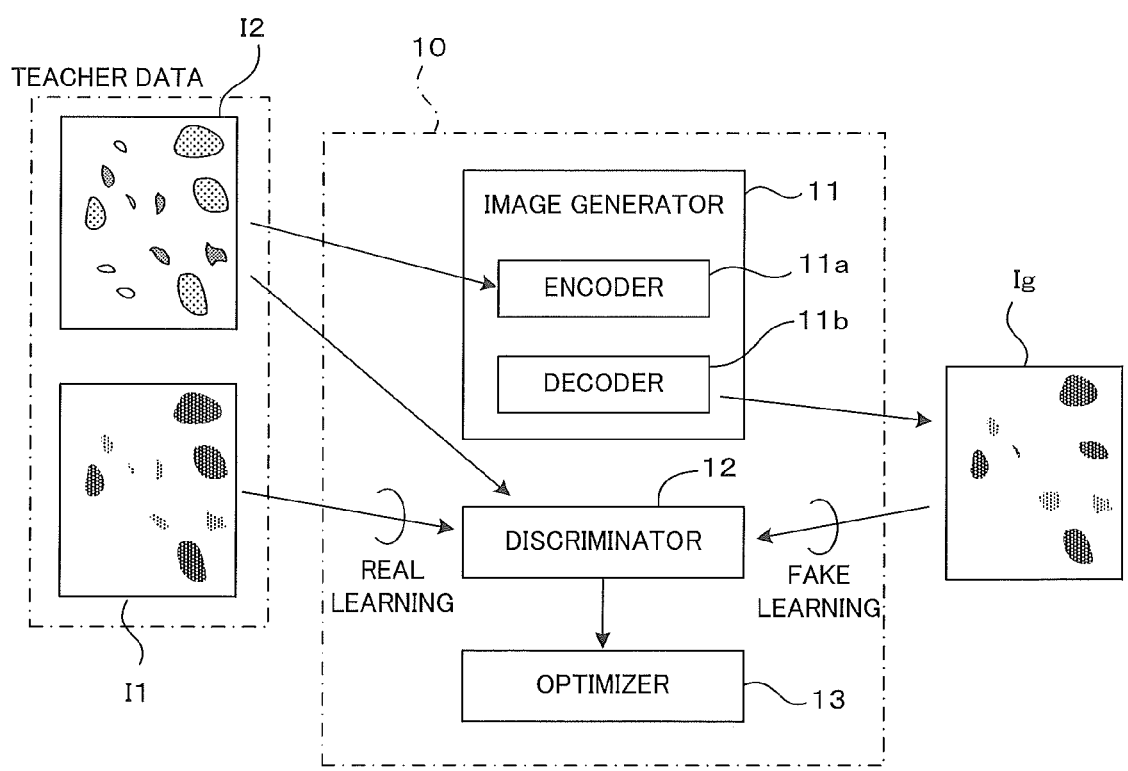
FIG. 4 is a diagram showing the operation of a learning model employed in this embodiment.

FIG. 4 is a diagram showing the operation of a pix2pix algorithm, which is a learning model employed in this embodiment. As shown in FIG. 4, the first learning model 10 includes an image generator 11, a discriminator 12 and an optimizer 13. The image generator 11 includes an encoder 11a for grasping an image characteristic by convolutional layers in a plurality of stages and a decoder 11b for generating an image by performing an inverse operation from the characteristic by inverse convolutional layers in the same number of stages. The second teacher image I2, which is a bright field image, is given as an input image to the image generator 11. The discriminator 12 discriminates from the image characteristic whether or not the input image is a generated image. The first teacher image I1, which is a fluorescence image, is input to the discriminator 12 to perform real learning. On the other hand, a generated image Ig output from the image generator 11 is input to the discriminator 12 to perform fake learning. The optimizer 13 adjusts internal parameters of the learning model so that the generated image Ig output by the image generator 11 approximates a real image (first teacher image I1). Learning progresses by repeating this. If learning sufficiently progresses, a function of generating a corresponding pseudo fluorescence image (intermediate image Im) from an unknown bright field image (test image It) is possessed.

Note that although fluorescent labeling is used as a method for administering a marker to a cell here, a mode of the marker is not limited to this. For example, a specific part may be selectively dyed with an appropriate dye. In this case, deep learning is performed using sets of an image of an undyed specimen and an image of a dyed specimen as teacher data. By doing so, it is possible to analogize and generate an image obtained when the specimen is dyed from a newly given undyed image.

Further, a plurality of types of markers may be introduced into one specimen. For example, calcein is known as a marker which is expressed in green in a cytoplasm of a living cell. Further, propidium iodide (PI) is known as a marker which is expressed in red in a nucleus of a dead cell. It is widely performed to introduce these into the same specimen. In such an example, the respective markers are expressed in different colors in a fluorescence image. Thus, living cells and dead cells can be distinguished by the color separation of an image, for example, in the case of a color image.

This technique can be introduced also into the image processing of this embodiment. Specifically, deep learning is performed using sets of a fluorescence image and a bright field image of the specimen having these two types of markers introduced thereinto as the teacher data. By doing so, an intermediate image is obtained in which, out of objects in the bright field image as the test image, those corresponding to living cells are shown in green corresponding to calcein and those corresponding to nuclei of dead cells are shown in red corresponding to PI.

Note that, in the case of introducing a plurality of types of markers having different luminous colors in this way, at least an image with a marker needs to be an image which can be handled with colors distinguished. For example, the data obtained by full-color imaging and color-separating into RGB colors can be used. Further, image data monochromatically captured via a band-pass filter corresponding to a luminous color may be handled as pseudo separation image data corresponding to this luminous color. If monochromatic imaging is performed, for example, using a highly sensitive cooled CCD camera, image data capable of color reproduction at a high resolution can be obtained.

As just described, by performing deep learning using the sets of the image with the marker and the image without the marker as the teacher data, the first learning model 10 is constructed. The thus constructed first learning model 10 analogizes a fluorescence image obtained when the marker is introduced into the same specimen based on the test image It, which is a new bright field image without a marker, and generates a pseudo image with a marker. This image is the intermediate image Im.

The intermediate image Im shown in FIG. 1 is a pseudo image with a marker corresponding to the test image It. Here, out of the objects included in the test image It, those in which two types of markers are expressed, are shown in two types of densities.

Referring back to FIGS. 1 and 2, the image processing is further described. By the process thus far, a pseudo image with a marker can be generated from an image obtained by imaging a specimen into which no marker is introduced. By selecting appropriate markers corresponding to aimed detected parts, the presence or absence of the detected parts in an image and the positions of the detected parts can be shown in the image. For example, if the test image It and the intermediate image Im are displayed in a superimposition manner, which of objects appearing in the test image It correspond to the detected parts can be easily visually confirmed. For example, in visually observing cells in an image, whether each cell is living or dead can be demonstrated. The objects not corresponding to the markers, i.e. those that are not observation objects, are excluded from the image at this point of time and do not affect a later process.

In an image with a marker, particularly a fluorescence image in which a marker becomes luminous in response to excitation light, information on the shapes of original objects are, in principle, lost in many cases. From this, information on the precise shapes and extents in the image of cells and the like may not be obtained also in a pseudo image with a marker output by the first learning model 10. For example, if a plurality of cells are in contact with or proximate to each other in a specimen, those cells possibly appear as an integral assembly in an image in some cases. This can become an error factor in quantitatively detecting the positions and number of the cells.

Accordingly, in this embodiment, the second learning model 20 is used to specify the positions of the detected parts from the intermediate image Im generated by the first learning model 10. As shown in FIG. 1, the second learning model 20 is constructed by performing deep learning using sets of a third teacher image I3 and a position information image Ip prepared in advance as teacher data. The position information image Ip is an image indicating the positions of representative points representing the detected parts in the corresponding third teacher image I3.

As described later, the second learning model 20 thus constructed has a function of detecting the positions of representative points representing the detected parts in an image from the image with a marker. In this sense, the second learning model 20 can also be called a "position determination model". In a specific processing, the intermediate image Im, which is a pseudo image with a marker corresponding to the test image It, is generated by the first learning model 10 as described above, and the intermediate image Im is input to the second learning model 20 (Step S104).

The second learning model 20 generates an image showing the positions of the representative points of the detected parts from the input intermediate image Im, and outputs this image as a result image Io (Step S105). For example, if the detected parts are "living cells" and the centroid positions of the nuclei of the living cells are representative points, the result image Io is an image showing the "centroid positions of the nuclei of the living cells", out of the objects included in the test image It. A result need not necessarily be output as an image in this way and may be, for example, output as data representing coordinates of the detected representative points. The definitions of the detected parts and the representative points are also arbitrary without being limited to the above.

If data for specifying the positions of the representative points of the detected parts in the image is obtained in this way, the number of the detected parts is easily automatically counted (Step S106) from that data. If a count result is output and presented to a user (Step S107), the user can obtain the count result of the detected parts included in the image only by preparing the test image It.

Figure 5:
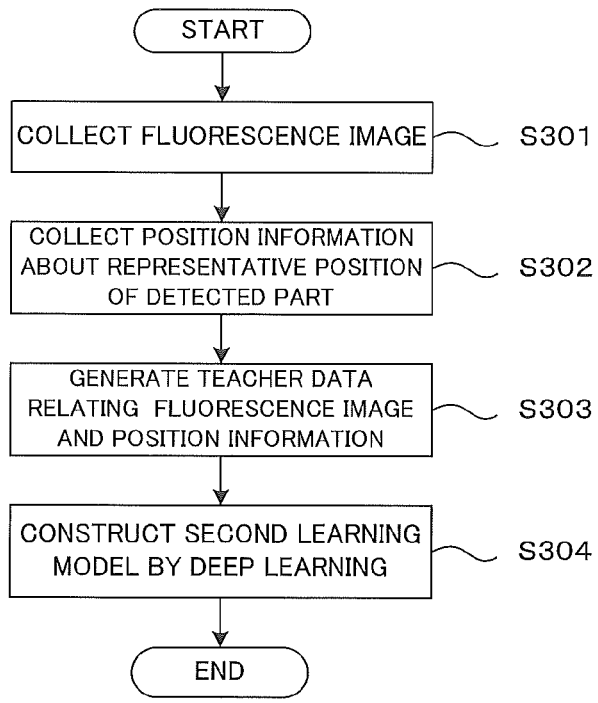
FIG. 5 is a flow chart showing a learning process for constructing the second learning model.

FIG. 5 is a flow chart showing a learning process for constructing the second learning model. A plurality of fluorescence images, which will become teacher images (third teacher images I3 shown in FIG. 1), are collected in advance (Step S301). A fluorescence image in this case may be either one of:

(1) The same fluorescence image as that collected as the first teacher image I1, and (2) The fluorescence image captured separately from the first teacher image I1.

Further, if an image with a pseudo marker generated by the first learning model 10 exhibits a sufficiently high degree of similarity to an actual fluorescence image, it is also possible to use:

(3) The pseudo fluorescence image output by the first learning model 10. Further, these fluorescence images may be combined into a teacher image.

Note that, although the teacher image is a fluorescence image here, the teacher image may be, in a broader definition, an image in which the same type of marker is expressed for the same type of detected parts as an image with a pseudo marker output by the first learning model 10.

Information (position information) for specifying the positions of the representative points is collected for the detected parts included in the collected fluorescence images (Step S302). For example, detected parts such as a specific type of cells or structures (e.g. cell nuclei) in the cells have a certain extent in an image, and the shapes thereof have large individual differences. Thus, it is difficult to uniquely represent the positions of the detected parts by simple data. Accordingly, the representative points of the detected parts are appropriately determined and the positions of the detected parts are represented by the positions of the representative points.

For example, if a detected part is a relatively small structure such as a cell nucleus, mitochondrion or the like in a cell, an appropriate position (e.g. centroid position) of this structure in the image can be set as a representative point. Also when an individual cell is a detected part, the centroid position of a nucleus thereof can be set as a representative point. By doing so, even if a plurality of proximate cells are, for example, shown as an integral assembly in a fluorescence image, it is shown that these cells are separate cells since a plurality of nuclei are included if the positions of the nuclei are specified. Specifically, it is possible to distinguish a plurality of cells appearing to be an integral assembly in a fluorescence image and individually count these cells.

To enable this, the positions of the representative points are set for the detected parts included in each of the collected fluorescence images. For example, the representative points may be set by causing a fluorescence image as a typical example to be displayed on a screen and causing a skilled person to designate and input the positions of the representative points. Further, a center or centroid of a relatively small structure demonstrated by a marker such as a cell nucleus may be obtained by an image processing and the position thereof may be set as the position of a representative point. Further, a known image processing (erosion processing) of shrinking objects included in a fluorescence image step by step may be performed and finally remaining points may be set as representative points. For example, a known MaxPooling processing can be suitably applied as an image processing for selecting one representative point from a region having an extent in this way.

Sets of the fluorescence image and the position information of the representative points of the detected parts included in the fluorescence image collected in this way are set as the teacher data (Step S303). In FIG. 1, this position information is shown as the image Ip mapping the positions of the representative points. However, without limitation to this, the position information may be represented in the form of a table describing, for example, the position coordinates of the representative points.

By performing deep learning based on the generated teacher data, the second learning model 20 is constructed (Step S304). For example, learning is performed with the third teacher image I3, which is a fluorescence image, corresponding to an input and the position information image Ip showing the positions of the representative points corresponding to an output. By doing so, the positions of the detected parts can be detected from the fluorescence image in which the marker corresponding to the detected parts is expressed.

Specifically, the second learning model 20 constructed as described above obtains a function of, if the intermediate image Im output by the first learning model 10 or a newly obtained unknown fluorescence image is input, outputting an image showing the detected parts in the input image by the positions of the representative points. This output image serves as the result image Io. Note that the purpose of processing is sufficient if the positions of the detected parts are specified. In that sense, instead of or in addition to the generation of the result image Io showing the positions of the representative points, a table or list representing the position coordinates of the detected representative points may be, for example, generated.

Figure 6A:
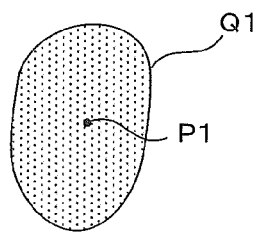
FIG. 6A is a diagram illustrating how to give representative points.
Figure 6B:
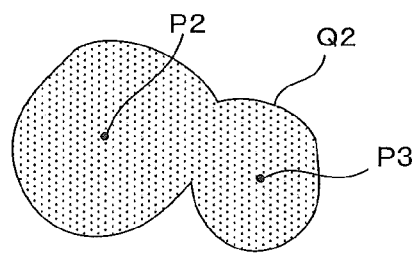
FIG. 6B is a diagram illustrating how to give representative points.

FIGS. 6A and 6B are diagrams illustrating how to give representative points. As shown in FIG. 6A, an object Q1 having a relatively simple shape can be, for example, thought to correspond to one independent cell (or cell mass). Accordingly, one representative point P1 may be set inside. On the other hand, as shown in FIG. 6B, if an object Q2 has a complicated outer peripheral shape, it is regarded that a plurality of cells are partially in contact. Accordingly, a plurality of representative points P2, P3 may be set according to that shape.

Even such cell coupling can also be dealt with by preparing teacher data as a collection of various case data and constructing the second learning model 20 by deep learning. Specifically, when objects having a similar shape appear in an unknown fluorescence image or the intermediate image Im output by the first learning model 10, those objects are not erroneously recognized as a single cell and representative points are respectively detected to correspond to the individual cells.

As just described, the second learning model 20 is suitable for the purpose of specifying the positions of the representative points of the detected parts from the intermediate image Im output from the first learning model 10 in this embodiment. Not only that, the second learning model 20 can be applied for the purpose of more generally detecting the positions of specific parts from a fluorescence image. For example, the second learning model 20 can be used for the application of automatically counting the positions or number of specific parts such as cells based on a fluorescence image of a specimen into which a marker emitting fluorescence is introduced. A learning algorithm is similar to that of the aforementioned first learning model 10.

As described above, the shapes of cells may not clearly appear in a fluorescence image. This makes it difficult to automatically count the positions or number of the cells from the fluorescence image and causes a problem of making it difficult to improve the accuracy of a count result. The second learning model 20 can solve this problem.

Note that a learning model in the case of evaluating a specimen on which such a drug as to affect cells is acted as described later is desirably constructed using a plurality of images obtained by imaging specimens prepared at various drug concentrations as teacher images. Depending on the action of the drug, morphological features of the cells change and the magnitudes of the changes depend on the drug concentration. Thus, a learning model constructed, for example, using only images of specimens having low drug concentrations is not necessarily effective also for images of specimens having high drug concentrations. The same applies also the other way around. If an image group in which images of specimens having various drug concentrations are mixed is used as a group of teacher images, the constructed learning model can also deal with specimens having various drug concentrations.

Figure 7:
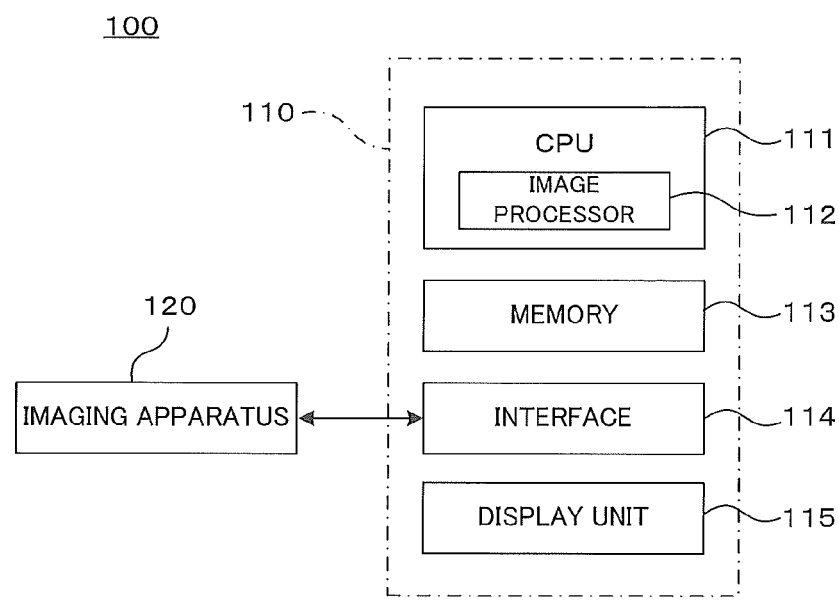
FIG. 7 is a block diagram showing an example of an apparatus configuration capable of performing the image processing of this embodiment.

FIG. 7 is a block diagram showing an example of an apparatus configuration capable of performing the image processing of this embodiment. This apparatus is an example of an image processing system capable of performing an image processing method according to the invention. The image processing system 100 includes an image processing apparatus 110 and an imaging apparatus 120. The image processing apparatus 110 is one embodiment of an image processing apparatus according to the invention and includes a CPU (Central Processing Unit) 111 with a built-in image processor 112, a memory 113, an interface 114 and a display unit 115.

The CPU 111 performs the image processing process and deep learning described above by executing a predetermined control program stored in advance in the memory 113. A processing for image data in this process is performed by the image processor 112. The memory 113 stores the control program to be executed by the CPU 111 and data generated by processing. The interface 114 is in charge of data communication with an external device. The interface 114 also receives an operation input from the user via an unillustrated input device (e.g. keyboard, mouse or the like). The display unit 115 displays and outputs a progress and a result of the process and notifies them to the user.

The imaging apparatus 120 is, for example, a microscope device provided with an imaging function. The imaging apparatus 120 generates image data by imaging a specimen such as cells cultured in a well plate and transmits the image data to the interface 114 of the image processing apparatus 110. If the imaging apparatus 120 is provided for the purpose of capturing the test image It, the imaging apparatus 120 may have a bright field imaging function. On the other hand, if the imaging apparatus 120 is provided for the purpose of collecting the first and second teacher images I1, I2, the imaging apparatus 120 may have a fluorescence imaging function in addition to the bright field imaging function. It is desirable that bright field imaging and fluorescence imaging can be performed in the same field of view for one specimen.

Note that the configuration of the image processing system is not limited to the above one, and the image processing apparatus 110 and the imaging apparatus 120 may be, for example, integrally configured. Further, if a library of image data captured in the past (for example, by reception via the interface 114) can be, for example, utilized, the image processing system 100 may not have the imaging function.

A practical example of the image processing configured as described above is described below. The inventors of this application conducted various evaluation experiments to verify the effectiveness of the image processing of this embodiment. Because of that, a result was obtained which indicated that this process was effective to automatically measure the positions and number of cells from an image. A part of that result is described below.

Figure 8:
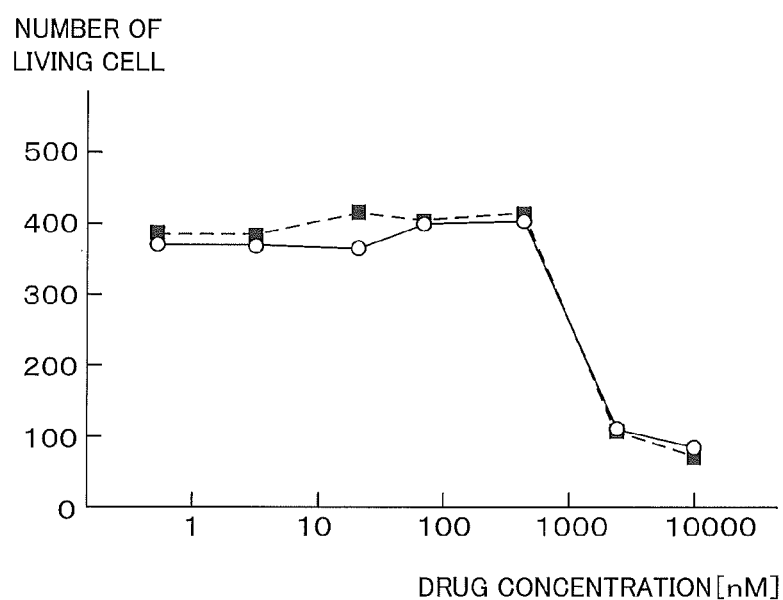
FIG. 8 is a graph showing an example of a measurement result on the number of cells according to this embodiment.

FIG. 8 is a graph showing an example of a measurement result on the number of cells according to this embodiment. The inventor of this application conducted an experiment to count the number of living cells by introducing Hoechst33342 (hereinafter, abbreviated as "Hoechst") and PI, each of which is a marker for dyeing cell nuclei, into HeLa cells and using a specimen on which a proteasome inhibitor (MG132) was acted at various concentrations. Here, Hoechst causes the nuclei of the cells to emit blue light in a fluorescence image regardless of whether the cells are living or dead, whereas PI causes the nuclei of the dead cells to emit red light. From this, the number of the living cells was calculated by subtracting the number of the cell nuclei counted in a red (R) image (number of the dead cells) from the number of the nuclei counted in a blue (B) image (total number of the living cells and the dead cells).

In FIG. 8, a solid line shows an example of the result of specifying and counting the positions of the cell nuclei using the first and second learning models 10, 20 using an image obtained by the bright field imaging of a specimen as a test image It. Further, a broken line shows an example of the result of specifying and counting the positions of the cell nuclei by directly inputting an image obtained by the fluorescence imaging of the same imaging range of the same specimen to the second learning model 20. As is understood from this, two results substantially match at each drug concentration. A similar comparison was made for a plurality of specimens, and a similar result was obtained in any of those cases.

From this, it is understood that an image with a pseudo marker (i.e. intermediate image Im), which is an output image obtained by inputting a bright field image (i.e. test image It) to the first learning model 10, has a high similarity to an image with a marker (fluorescence image) captured with the marker actually introduced.

Figure 9A:
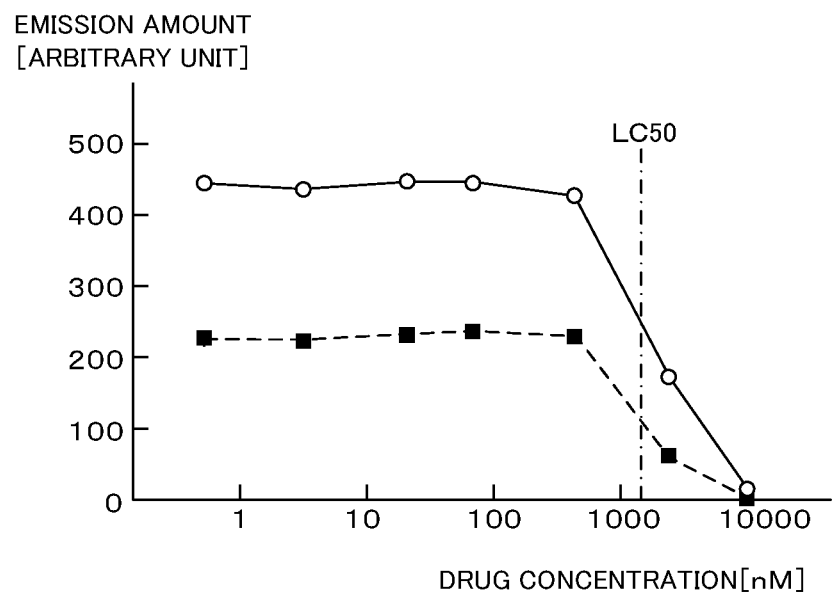
FIG. 9A is a graph comparing the measurement result on the number of the cells by this embodiment to an ATP assay method.
Figure 9B:
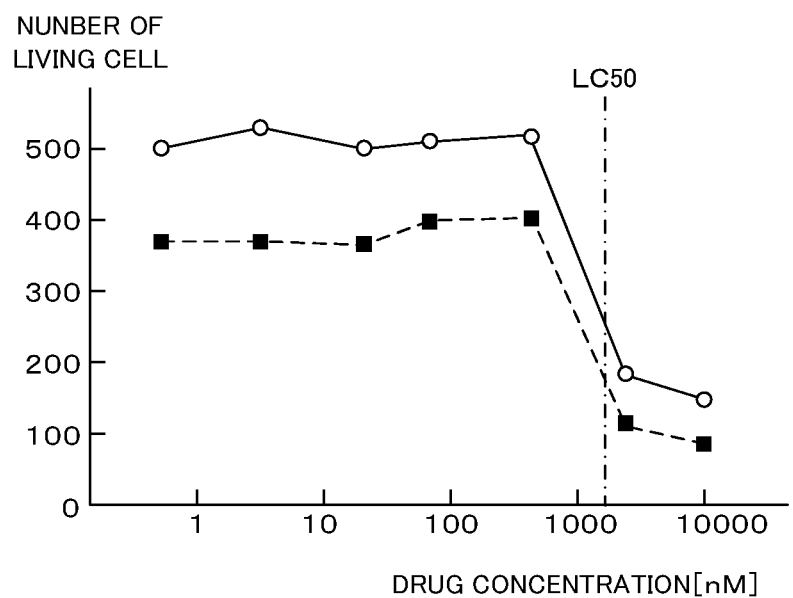
FIG. 9B is a graph comparing the measurement result on the number of the cells by this embodiment to an ATP assay method.

FIGS. 9A and 9B are graphs comparing the measurement result on the number of the cells by this embodiment to an ATP assay method. FIG. 9A shows an example of a result of evaluating the quantity of living cells by a known ATP assay method for specimens on which a drug was acted at various concentrations as in FIG. 8. On the other hand, FIG. 9B shows an example of a result of counting the number of living cells of a specimen, into which Hoechst and PI were introduced, by this embodiment. In these, a solid line shows a case where 5000 cells were seeded in one well and a broken line shows a case where 2000 cells were seeded in one well. Note that since the result of FIG. 9B is a count result in an image obtained by imaging a partial region of one well, that count result does not indicate a total number of the cells in the well.

From these results, a median lethal concentration (LC 50) generally used as an index of drug effects was obtained for each method. In either method, substantially the same result was obtained. A similar comparison was made for a plurality of specimens, and a similar result was obtained in any of those cases. This indicates that the count result on the number of the cells by this embodiment matches reality well and the obtained evaluation of drug efficacy based on the count result is equivalent to a result by the ATP assay method. Further, a similar evaluation was made also for HepG2 cells and confirmed that an LC50 value obtained from the count result of this embodiment and an LC50 value obtained by the ATP assay method matched well.

Specifically, it can be said that the position detection of the cells and the count of the number of the cells based on the position detection by this embodiment can be utilized as a quantitative method equivalent to the ATP assay method widely used as a standard quantitative method. The ATP assay method is invasive for cells such as by dissolving the cells, whereas the method of this embodiment is more advantageous in that this method is capable of quantifying cells from a bright field image not using a marker or the like and is non-invasive.

FIGS. 10 and 11 are pictures showing image examples of triply dyed specimens. Out of these, FIG. 10 shows image examples when HepG2 cells were used as a specimen and FIG. 11 shows image examples when Hela cells were used as a specimen. It is described below using these images that a pseudo fluorescence image (i.e. intermediate image Im) generated by the first learning model 10 of this embodiment has a high similarity to a true fluorescence image.

Three types of markers, i.e. calcein, Hoechst and PI are introduced as fluorescent markers into each specimen. When a color image obtained by imaging the specimen is color-separated into RGB three primary colors, fluorescence by calcein appears in a green (G) image, fluorescence by Hoechst appears in a red (R) image and fluorescence by PI appears in a blue (B) image. In a full-color image obtained by merging three monochromatic images, the cytoplasms of living cells are shown in green and the nuclei thereof are shown in blue. On the other hand, the nuclei of dead cells dyed with both Hoechst and PI show a color close to a pink color in the color image by the overlap of red and blue colors. Therefore, whether the cells are living or dead can be discriminated from the colors of the nuclei.

By color-separating a full-color image obtained by the fluorescence imaging of the specimen into RGB three primary colors and inputting image data to the first learning model 10 constructed for each color in advance, intermediate images of the respective RGB colors are obtained. By synthesizing (merging) those images, a full-color pseudo fluorescence image is obtained. The pseudo fluorescence image obtained in this way and a true fluorescence image obtained by the fluorescence imaging of the same specimen were compared. Note that such a full-color pseudo fluorescence image is also obtained by inputting image data to the first learning model 10 constructed with full-color images as teacher images.

When the images shown in FIGS. 10 and 11 are seen along a horizontal arrangement direction, each image on a left end is a bright field image serving as an input image to the first learning model 10. Further, a middle image is an image generated by inputting the image on the left end to the first learning model 10, i.e. the intermediate image Im. Further, an image on a right end is a fluorescence image obtained by actual fluorescence imaging of the same specimen.

An ideal operation of the first learning model 10 used in the image processing of this embodiment is to output the same image as the color image on the right end when the bright field image on the left end is input. In this sense, the color image on the right end can be said to be a target image to be output by the first learning model 10.

In these figures, the images in upper two stages are example of specimens not administered with a drug. More specifically, row A corresponds to examples of images used as teacher data in deep learning, and row B corresponds to images not used in the teacher data. Further, rows C and D show examples of specimens administered with a drug. Out of these, row C corresponds to examples of images used as the teacher data in deep learning and row D corresponds to images not used in the teacher data.

In either of FIGS. 10 and 11, if the generated image (pseudo fluorescence image) in the middle generated and output based on a result of learning by the first learning model 10 to which the input image was given is compared to the target image on the right end, which is an image obtained by actual fluorescence imaging of the specimen in each row, the positions, sizes, brightnesses and the like of luminous points indicating the positions of the cell nuclei match very well. This is the same as with not only the input images used in learning as the teacher data, but also input images not used in learning, i.e. unknown to the first learning model 10.

Further, although the colors of the images are not shown in FIGS. 10 and 11, the colors of the generated images and those of the target images also match well. Specifically, in the images of rows A and B corresponding to the specimens to which a drug is not added, the arrangements of blue images indicating the nuclei of the living cells and green images indicating the cytoplasms of the living cells match well between the generated images and the target images. Further, in the images of rows C and D corresponding to the specimens added with the drug, pink images are also included in addition to blue and green images to correspond to an increase of the dead cells due to the action of the drug. Those arrangements also match well between the images.

From these, the pseudo fluorescence image output as the intermediate image Im in the image processing of this embodiment can be said to be sufficiently utilizable as an alternative to the fluorescence image obtained by actual fluorescence imaging. Further, when the numbers of the cell nuclei were counted by inputting the image used in the teacher data and the generated image obtained using the former image as the input image respectively to the second learning model 20, those count results also matched well.

Further, the accuracy of the image processing process of this embodiment including an output by the second learning model 20 is demonstrated by the following experiment result. In an experiment, the number of cell nuclei obtained by performing the image processing of this embodiment using a bright field image as an input image and the number of cell nuclei obtained by giving a fluorescence image obtained by actual fluorescence imaging to the second learning model 20 instead of the intermediate image Im were compared.

Specifically, a specimen was prepared in which calcein as a marker was introduced into HepG2 cells, and a bright field image and a fluorescence image of that specimen were captured. The number of cell nuclei (i.e. the number of the cells) was counted from a result obtained when the fluorescence image was given as an input to the second learning model 20. The number of the cells at this time is called a "correct image-derived number". Further, an intermediate image Im obtained by inputting a bright field image to the first learning model 10 was given as an input to the second learning model 20, and the number of the cells was counted from that result. The number of the cells at this time is called a "generated image-derived number".

Figure 12:
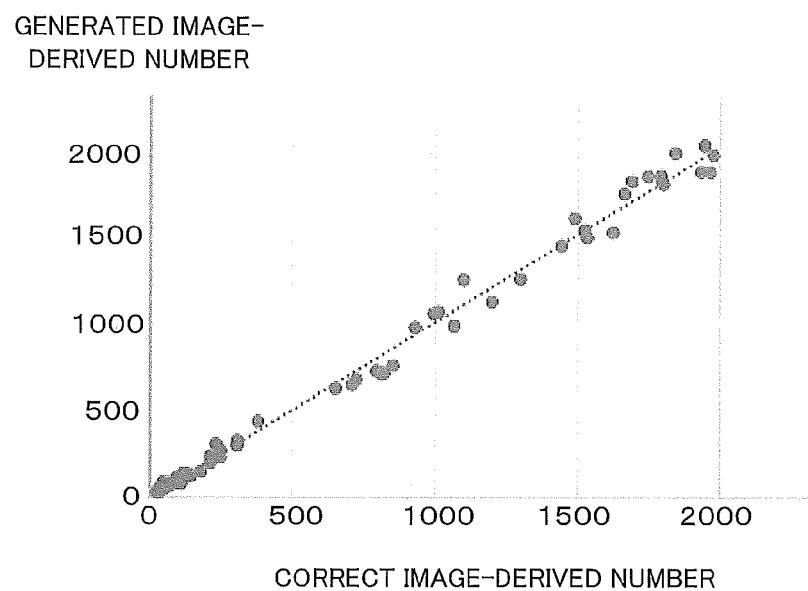
FIG. 12 is a graph showing an example of a result of an experiment comparing results of counting.

FIG. 12 is a graph showing an experiment result. As shown in FIG. 12, the correct image-derived number and the generated image-derived number showed a high degree of coincidence and straight line approximation by a least squares method was:

$$y=1.0196x-3.1554,$$

and a coefficient of determination $R^2$ was 0.994. From this, it is indicated that a combination of the marker generation model (first learning model 10) and the position determination model (second learning model 20) of this embodiment is suitable to count the number of cells from a bright field image.

The image processing method of this embodiment described above can be utilized in a drug sensitivity test method for examining influences of a drug on cells. An example of the drug sensitivity test method including the above image processing is described below.

Figure 13:
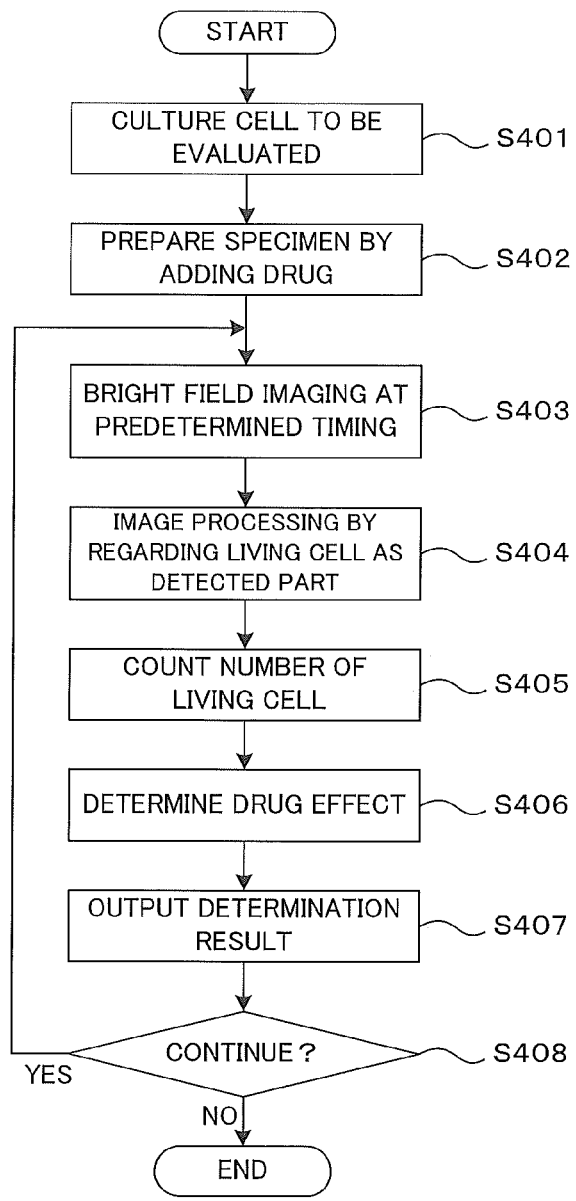
FIG. 13 is a flow chart showing the drug sensitivity test method to which the image processing method of this embodiment is applied.

FIG. 13 is a flow chart showing the drug sensitivity test method to which the image processing method of this embodiment is applied. First, cells to be evaluated are cultured (Step S401), and a specimen is prepared by adding a drug of a predetermined concentration (Step S402). A bright field image of the specimen is captured at a predetermined timing (Step S403), such as when a certain time elapses from the administration of the drug.

The above image processing is performed for the thus obtained bright field image. Specifically, the above image processing process is performed using the captured bright field image as a test image It and living cells as detected parts (Step S404), and the number of the living cells is counted (Step S405). The effects of the drug are determined, such as by obtaining the LC50 value described above from a count result (Step S406), and a determination result is, for example, output to the display unit 115 (Step S407). Further, in the case of continuing observation and regularly evaluating the specimen (Step S408), return is made to Step S403 and the specimen is repeatedly imaged and evaluated. Since the cells can be evaluated only by the bright field image without being processed in this embodiment, such a continuous evaluation is possible.

As described above, in this embodiment, the first learning model 10 constructed by deep learning using sets of a fluorescence image as an example of an image with a marker and a bright field image as an example of a corresponding image without a marker collected in advance as teacher data, and the second learning model 20 constructed by deep learning using sets of a fluorescence image and information representing the positions of detected parts in the fluorescence image as teacher data are prepared in advance.

If a bright field image as a test image It is input to the first learning model 10, the first learning model 10 outputs an image obtained by adding a marker to the test image It in a pseudo manner based on a learning result. That is, the first learning model 10 can generate an image, similar to the one in which a marker is expressed, from a bright field image without a marker. Thus, it is not necessary to introduce a marker beforehand, and an image with a marker can be obtained without invading the cells. Therefore, the specimen including the cells can be observed with time. Further, since an operation and a reagent for marker introduction are unnecessary, processing cost can also be reduced.

The second learning model 20 learns a relationship between an image with a marker and the positions of detected parts in the image. Accordingly, the second learning model 20 specifies and outputs the positions of the detected parts selected in advance from an actually captured image with a marker or an image with a pseudo marker output by the first learning model 10. A plurality of cells possibly appear to be in contact with each other or seemingly in contact by being overlapped in a depth direction in an image in some cases. By learning also such cases, those cells can be separated and processed. Therefore, the positions and number of the detected parts in the image can be precisely measured from the output of the second learning model 20.

As a result, in the above embodiment, the positions of detected parts in a bright field image can be accurately specified by inputting a test image It, which is an unknown bright field image, to the first learning model 10, processing the test image It, inputting that processing result to the second learning model 20 and processing the processing result. That detection result is suitable for the purpose of automatically measuring the positions and number of the detected parts.

As described above, in the above embodiment, the first teacher image I1, the second teacher image I2 and the third teacher image I3 respectively correspond to a "first image", a "second image" and a "third image" of the invention. Further, the interface 114 for receiving image data from outside in the image processing apparatus 110 of FIG. 7 functions as an "image acquirer" of the invention. Further, the CPU 111, particularly the image processor 112, functions as an "image processor" of the invention.

Note that the invention is not limited to the above embodiment and various changes other than the aforementioned ones can be made without departing from the gist of the invention. For example, the test image It and the second teacher image I2 are bright field images in the above embodiment. However, these may be images obtained by another non-invasive imaging method, e.g. phase difference images. Further, the first teacher image I1 and the third teacher image I3 are fluorescence images in the above embodiment. However, these may be other images with markers, e.g. images labeled by dyes which develop color under visible light illumination.

Further, the image processing apparatus 110 of the above embodiment is configured to receive image data given from an external device, e.g. image data obtained by imaging in the imaging apparatus 120, via the interface 114. However, the image processing apparatus itself may have an imaging function as described above. Specifically, the entire image processing system 100 can be regarded as the "image processing apparatus" of the invention. In this case, the imaging apparatus 120 for performing the imaging functions as the "image acquirer" of the invention. Further, if an image library of images captured in the past is present, it is also possible to generate teacher data from those images. In this case, the imaging function for the purpose of obtaining teacher images can be eliminated.

Further, a device for performing a processing for constructing first and second learning models and a device for processing a test image It utilizing a result of the former device may be, for example, different. For example, the first and second learning models 10, 20 constructed by deep learning in a certain image processing apparatus may be ported to another image processing apparatus, and the apparatus as a port destination may be configured to process a test image It. If learning models are constructed by an apparatus having a high computational power such as a supercomputer, highly accurate learning models can be constructed using a large quantity of data. On the other hand, the device for processing the test image It utilizing the constructed learning models needs not have a high computational power since it is sufficient to perform only a relatively simple computation. From this, a processing can be performed by a relatively simple computation device built in the apparatus.

Figure 14:
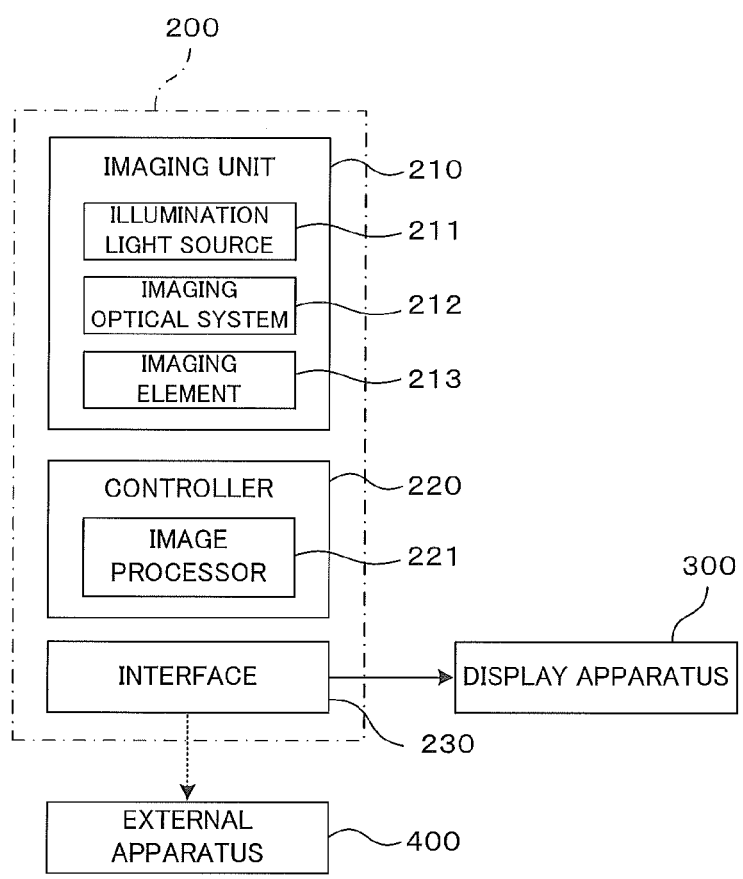
FIG. 14 is a diagram showing another embodiment of the invention.

FIG. 14 is a diagram showing another embodiment of the invention. More specifically, FIG. 14 is a block diagram showing a microscope apparatus 200, which is another embodiment of the image processing apparatus according to the invention. This microscope apparatus 200 is provided with a microscope imaging unit 210 including an illumination light source 211, an imaging optical system 212 and an imaging element 213, a controller 220 and a video interface (IF) 230. That is, this embodiment relates to a microscope apparatus having a video output function. The microscope imaging unit 210 may have a function of the bright field imaging or phase difference imaging of a specimen and needs not have a fluorescence imaging function.

The controller 220 has a function as a control body for controlling each part of the apparatus to perform an imaging operation. Further, the controller 220 applies an appropriate image processing to an image captured by the imaging unit 210 and outputs the processed image to the video interface 230. For this purpose, the controller 220 is provided with an image processor 221.

The image processor 221 is formed into a device by incorporating the above already learned first and second learning models 10, 20 as fixed or rewritable data into a dedicated hardware. For example, the image processor 221 can be configured by an ASIC (Application Specific Integrated Circuit), PLA (Programmable Logic Array), FPGA (Field Programmable Gate Array), GPU (Graphics Processing Unit) or the like. The image processor 221 has a function of outputting image data corresponding to an intermediate image Im generated by the first learning model 10 and an output image Io generated by the second learning model 20. The image processor 221 may also have a function of superimposing and synthesizing various images.

Image data obtained by imaging by the imaging unit 210 or image data after the obtained image data is processed by the image processor 221 is output to an external display apparatus 300 via the video interface 230. The display apparatus 300 displays and outputs an image corresponding to the image data given from the microscope apparatus 200. In this embodiment, the imaging unit 210 functions as the "image acquirer" of the invention, and the image processor 221 functions as the "image processor" of the invention. Instead of or in addition to the output to the display apparatus 300, a processing result may be output to an appropriate external apparatus 400 via the interface 230. An external storage device for storing the processing result, a computer apparatus for receiving the processing result and further performing an image processing or an analysis or the like can be employed as the external apparatus 400.

According to this configuration, images captured by the imaging unit 210 can be successively processed by the image processor 221 and displayed on the display apparatus 300. Here, if an intermediate image Im output by the image processor 221 is displayed on the display apparatus 300, the microscope apparatus 200 not having the fluorescence imaging function can be caused to function as a pseudo fluorescence microscope. Specifically, the microscope apparatus 200 has a function of outputting fluorescence images. If the constructed learning models are formed into a device in this way, a totally new function can be given, for example, by incorporating this device into an existing microscope apparatus. By using a dedicated hardware specialized in image processing, a time required for processing can be shortened. If a processing for one image can be, for example, completed within about 0.1 sec or less, it can be, in effect, said to be a real-time image processing.

For example, time-lapse imaging for intermittently imaging at a time interval substantially equal to the time required for image processing can be performed and an intermediate image Im can be displayed on the display apparatus 300 by performing the image processing every time. By doing so, a specimen can be observed substantially in real time by pseudo fluorescence images, similarly to a fluorescence microscope. Further, if the output image Io output by the second learning model 20 or a count result based on the output image Io is displayed on the display apparatus 300, a state of the specimen changing from moment to moment can be quantitatively grasped.

A learning model can be constructed, for example, using structures appearing only at a specific time in the activity of cells (e.g. chromosomes temporarily appearing in the process of cell division) as detected parts. By doing so, outputs suitable for the observation of cell division can be obtained. Specifically, if the intermediate image Im is displayed on the display apparatus 300, a corresponding characteristic marker appears in a pseudo fluorescence image, which is a displayed image, when the detected parts appear in the activity of cells. Thus, the appearance of the detected parts can be immediately grasped. Further, a cell cycle can be quantitatively tracked from a variation of a count result of such detected parts that appear only at a specific time of the cell cycle.

Such an application is possible if it is possible to use a marker for selectively dyeing parts which temporarily appear in each stage of the activity of cells and collect a sufficient number of images, in which the marker is expressed, as teacher images. Specifically, by constructing a learning model using such images with the marker and corresponding bright field images or phase difference images as teacher data and inputting a bright field image or phase difference image for a specimen without the marker to the learning model, various pieces of information on properties of cells such as whether the cells are living or dead and the cell cycle can be obtained.

Further, if a learning model is constructed, for example, using images of a specimen with a marker which is differently expressed in undifferentiated cells and differentiated cells as teacher images, the undifferentiated cells and the differentiated cells can be discriminated from images of the specimen into which the marker is not introduced. Then, quantitative information suitable for the observation of a cell differentiation process such as individual counts of those cells can be obtained.

As the specific embodiments have been described above, at least parts of a plurality of first images may be, for example, used as at least parts of a plurality of third images in this invention. Alternatively, the plurality of first images and the plurality of third images may be, for example, different from each other. Further, for example, an output image when a second image is input to the first learning model may be a third image. Further, third images obtained in different methods may be mixed. As just described, images obtained by various methods can be used as the third images and the collection of many cases is suitable to enhance the effects of learning.

Further, for example, the test image and the second image may be bright field images or phase difference images. Images in which a marker is not expressed can be used as the test image and the second image. Thus, the test image and the second image may be obtained by imaging a specimen into which a marker is not introduced. If bright field images or phase difference images are used as such images, a high affinity for visual observation can be obtained.

Further, the first image may be, for example, a fluorescence image obtained by imaging fluorescent-labeled cells under excitation light illumination. In a fluorescent labeling technology, many techniques for selectively expressing a marker in specific parts of cells according to a purpose have been developed. By applying such an established technique, aimed detected parts can be reliably detected.

Here, fluorescent labeling showing different expression modes between living cells and dead cells may be performed. By such a configuration, living cells and dead cells can be discriminated from an image without introducing a marker.

Further, the image processing method according to the invention may be, for example, configured to count and output the number of detected parts based on a result image. Since the positions of representative points of the detected parts are detected according to the invention as described above, even if a plurality of the detected parts having an extent in the image are overlapped for example, those detected parts can be individually detected. From this, the number of the detected parts itself can be automatically counted by counting the number of the detected representative points.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

INDUSTRIAL APPLICABILITY

Since this invention can specify the positions of specific parts in an image including cells in a non-invasive manner, it is suitable for the observation of a specimen including cells with time. Thus, this invention is particularly suitable, for example, for applications such as a drug sensitivity test for examining effects of a drug for cells and drug discovery screening, such as for anticancer drugs based on the drug sensitivity test.

REFERENCE SIGNS LIST 10 first learning model
20 second learning model
100 image processing system
110 image processing apparatus
111 CPU
112 image processor
114 interface (image acquirer)
120 imaging apparatus (image acquirer)
200 microscope apparatus (image processing apparatus)
210 imaging unit (image acquirer)
221 image processor (image processor)
I1 first teacher image (first image)
I2 second teacher image (second image)
I3 third teacher image (third image)
Ip position information image
Im intermediate image
Io result image
It test image

The invention claimed is:

1. An image processing method for detecting a position of a detected part which is specific from a test image obtained by imaging a cell, the image processing method comprising:
generating an image which is corresponding to the test image and in which a pseudo marker is attached as an intermediate image by inputting the test image in which a marker corresponding to the detected part is not expressed to a first learning model and;
generating an image in which the position of the detected part is indicated by a representative point thereof by inputting the intermediate image to a second learning model and outputting the image as a result image, wherein:
the first learning model is constructed by using teacher data associating a first image and a second image captured to include a same cell and performing deep learning with the second image corresponding to an input and the first image corresponding to an output, the first image being an image in which the marker is expressed and the second image being an image in which the marker is not expressed; and
the second learning model is constructed by using teacher data associating a third image, which is captured to include a cell and in which the marker is expressed, and information representing a position of the representative point included in the third image and performing deep learning with the third image corresponding to an input and the position of the representative point corresponding to an output.

2. The image processing method according to claim 1, wherein at least parts of a plurality of first images is used as at least parts of a plurality of third images.

3. The image processing method according to claim 1, wherein a plurality of first images and a plurality of third images are different from each other.

4. The image processing method according to claim 1, wherein an output image from the first learning model when the second image is input to the first learning model is the third image.

5. The image processing method according to claim 1, wherein the test image and the second image are bright field images or phase difference images.

6. The image processing method according to claim 1, wherein the first image is a fluorescence image obtained by imaging fluorescent-labeled cells under excitation light illumination.

7. The image processing method according to claim 6, wherein fluorescent labeling showing different expression modes between living cells and dead cells is performed.

8. The image processing method according to claim 1, further comprising counting and outputting a number of detected parts based on the result image.

9. A drug sensitivity test method, comprising:
obtaining an image by imaging a specimen to which a drug to be evaluated is administered to cultured cells;
counting a number of living cells as the detected parts by the image processing method according to claim 8 using the image obtained by the imaging as the test image; and
determining sensitivity of the cells to the drug based on a result of counting.

10. An image processing apparatus for detecting a position of a detected part which is specific from a test image obtained by imaging a cell, the image processing apparatus comprising:
an image acquirer which obtains a bright field image or phase difference image in which a marker corresponding to the detected part is not expressed as the test image; and
an image processor which performs an image processing to generate an image which is corresponding to the test image and in which a pseudo marker is attached as an intermediate image by inputting the test image to a first learning model and an image processing to generate and output an image in which the position of the detected part is indicated by a representative point thereof as a result image by inputting the intermediate image to a second learning model, wherein:
the first learning model is constructed by using teacher data associating a first image and a second image captured to include a same cell and performing deep learning with the second image corresponding to an input and the first image corresponding to an output, the first image being an image in which the marker is expressed and the second image being an image in which the marker is not expressed; and the second learning model is constructed by using teacher data associating a third image, which is captured to include a cell and in which the marker is expressed, and information representing a position of the representative point included in the third image and performing deep learning with the third image corresponding to an input and the position of the representative point corresponding to an output.

\* \* \* \* \*